United States Patent [19]

Moser

[11] 3,932,762
[45] Jan. 13, 1976

[54] APPARATUS FOR MEASURING RADIATION ANGLE DEPENDENCE

[75] Inventor: Herbert Moser, Leopoldshafen, Germany

[73] Assignee: Gesellschaft für Kernforschung m.b.H., Karlsruhe, Germany

[22] Filed: July 29, 1974

[21] Appl. No.: 492,923

[30] Foreign Application Priority Data
July 28, 1973  Germany............................ 2338481

[52] U.S. Cl. ............... 250/574; 250/227; 356/102; 356/103
[51] Int. Cl.² .................. G01N 15/02; G01N 21/26
[58] Field of Search ................... 250/227, 564, 574; 356/102, 103, 37; 350/63, 96 B

[56] References Cited
UNITED STATES PATENTS

| | | |
|---|---|---|
| 3,508,830 | 4/1970 | Hopkins et al...................... 356/103 |
| 3,535,531 | 10/1970 | Neitzel............................... 250/574 |
| 3,609,043 | 9/1971 | Simmons et al. .................. 356/102 |
| 3,769,633 | 10/1973 | Tetter........................... 250/213 VT |
| 3,770,351 | 11/1973 | Wyatt ................................ 356/102 |
| 3,819,940 | 6/1974 | Laws................................. 250/227 |
| 3,835,315 | 9/1974 | Gravitt, Jr....................... 250/227 X |

*Primary Examiner*—James W. Lawrence
*Assistant Examiner*—E. R. LaRoche
*Attorney, Agent, or Firm*—Spencer & Kaye

[57] ABSTRACT

Apparatus for measuring the angular dependence of radiation scattered from a volume, including a local resolution radiation detector having a radiation-sensitive surface, and an optical system directing the radiation onto the radiation-sensitive surface in such a manner as to establish a single-value relationship between the angular direction of radiation from the volume and the location of impingement thereof on the radiation-sensitive surface.

8 Claims, 2 Drawing Figures

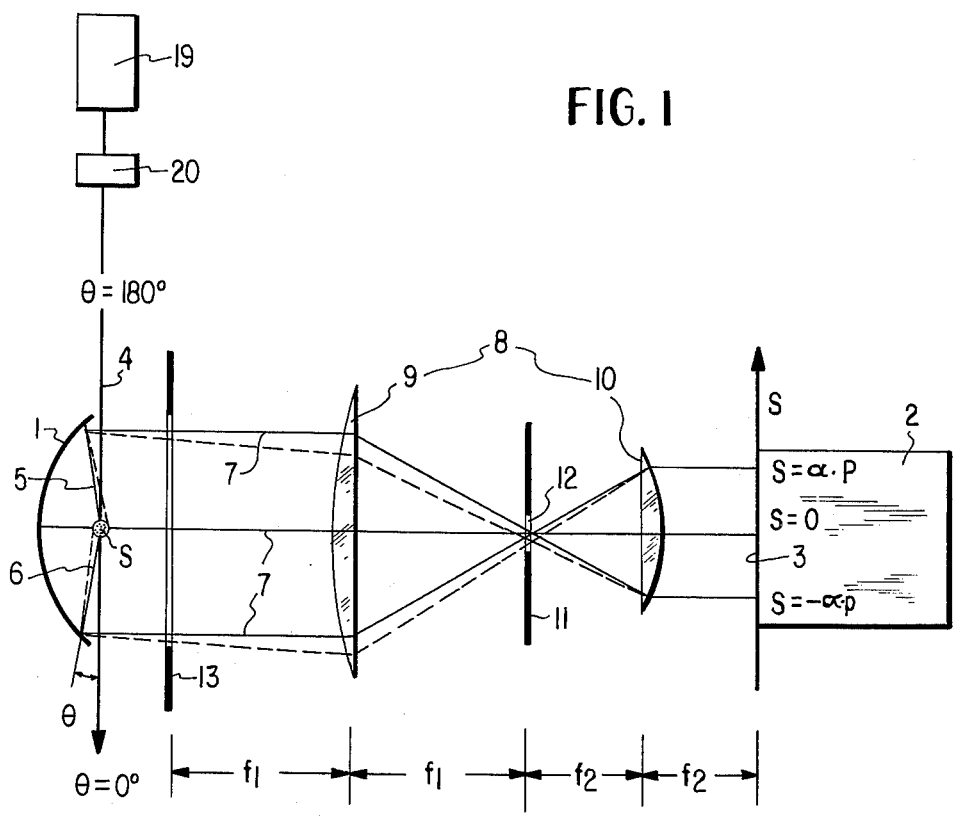
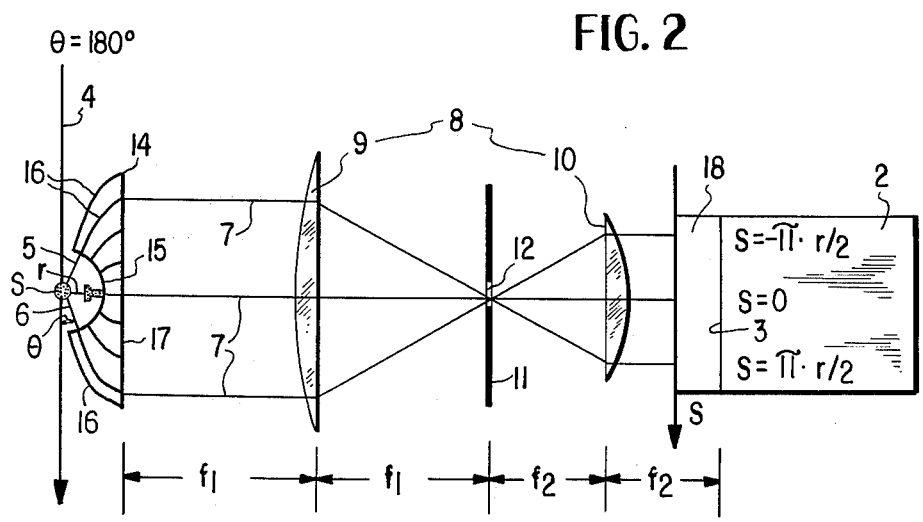

ic volume S, the angular resolution of the apparatus.

APPARATUS FOR MEASURING RADIATION ANGLE DEPENDENCE

BACKGROUND OF THE INVENTION

The present invention relates to an apparatus for measuring radiation angle dependence of scattered light, and particularly to apparatus capable of achieving very short time resolutions.

Apparatus is already known for measuring the angular dependence of light scattered from small particles, as described, for example, in J. Chem. Phys. 51, 1931 (1969). In this apparatus a laser beam is directed onto a narrow stream of particles at a constant angle and the angular dependence of the scattered radiation is measured with the aid of a detector fastened to an arm which is pivotal about the scattering volume. The measurement of this angular dependence then makes it possible to determine the size of the particles contained in the scattering volume.

Because, at the present day, the angular dependence of light scattered from small particles is to be recorded as a function of rapidly varying parameters or during very short time intervals, there is a need for a method which can take measurements in very short periods. With commercially available apparatus of the type described above the measurement of the angular dependence of the scattered light intensity of a suspension, for example, takes about 1 minute. For reasons of stability, the measurement time cannot be reduced by increasing the speed of rotation of the detector about the scattering volume by several orders of magnitude.

However, in many technical areas there is an increasing need for a much faster method, for example, for measuring short-time changes in the size of the droplets during formation of a fog, or the dependency of the cluster size upon inlet parameters, the monitoring of production in the manufacture of fibers, dies or colloids, testing of emulsification and coagulation processes, recording of the local and/or time variation in the size of aerosol particles in air, exhaust emission control for automobiles, examination of bacteria or rapid analysis of series thereof, analysis of the ejected matter in colloid drive mechanisms and measuring the change in size of plasma clusters. Particularly these last-mentioned measurements of changes in time require a method capable of making measurements in the nanosecond range.

SUMMARY OF THE INVENTION

It is an object of the present invention to measure the complete light angular dependence in as short a measuring time as possible.

This problem is solved, according to the present invention, by disposing optical elements to conduct the radiation divergently emanating from a radiating volume onto the radiation-sensitive surface of a local resolution radiation detector in such a manner as to establish an unequivocal correspondence between the radiation scattering angle and the locus of the radiation appearing on that surface.

Time resolution can be achieved either by pulsing the radiation source or by actuation of an electronic shutter in the local resolution radiation detector. A parabolic mirror whose focal point coincides with the locus of the scattering volume can be used for this purpose, where the parabolic mirror encloses the scattering volume over an angle of about 180°, transforming the scattered light into a collimated beam, while a lens system optically reproduces this collimated beam on the radiation-sensitive surface.

According to a further embodiment of the present invention, a cylindrical surface whose center of curvature coincides with the locus of the scattering volume encloses the scattering volume over an angle of about 180°, individual radiation conducting fibers are connected to that surface and are disposed to optically transform the cylindrical surface into a plane, and a lens system reproduces the collimated beam emanating from that plane on the radiation-sensitive surface. In a preferred form of construction of this embodiment of the invention, the radiation conducting fibers may be light conductive fibers and the beam to produce the scattered light may be a laser beam, for example.

BRIEF DESCRIPTION OF THE DRAWING

FIGS. 1 and 2 are pictorial views of two preferred embodiments of the invention.

DESCRIPTION OF THE PREFERRED EMBODIMENTS

A significant component of the apparatus for measuring particularly the scattered light angular dependence according to the invention by means of a parabolic mirror 1 and an optical multi-channel analyzer 2 is the multi-channel analyzer 2 shown in FIG. 1 as the local resolution radiation detector. The analyzer is a vidicon tube whose light-sensitive surface 3 is not homogeneously sensitive but is divided into approximately 500 parallel, juxtaposed, slit-type surface elements giving a total area of 12.5 × 9 mm² e.g., an Optical Multichannel Analyzer (OMA) of SSR Instruments, Santa Monica, Calif., USA. To this planar surface, the output of an optical system (to be described below) is applied and this output is thus resolved into 500 intervals. The conversion of the stored information is effected, as usual, by scanning with an electron beam. The resulting current pulses are processed by an appropriate electronic system not shown in detail.

In the scattered light measurements effected with the aid of the present invention the information is obtained as energy current density $I(\theta)$ as a function of the scattering angle $\theta$. $I(\theta)$ could also be measured by detectors arranged on a cylindrical jacket. Since a vidicon tube is planar, however, a suitable optical arrangement must effect the transformation from the cylindrical surface to the plane. An advantageous arrangement for achieving this is shown in FIG. 1.

Referring to FIG. 1, a scattering medium S, for example a volume of certain size with small particles which may be contained in a vessel or as a component of a flowing stream of particles, is illuminated by a stationary laser beam 4. The scattered light, e.g., the partial beams 5 and 6, divergently emanating from the scattering volume S is transformed into a collimated beam 7 by a parabolic mirror 1 whose focal point coincides with the location of the scattering volume S. The diameter of this light beam 7 is modified by a telescope 8 including the optical lenses 9 and 10 to match the dimensions of the image window, or entrance aperture, 3 of the vidicon 2.

An aperature 11 is disposed to block essentially all of the scattered light which might travel directly to the vidicon 2, i.e. without reflection at the parabolic mirror 1. The size of the opening 12 in aperture 11 also determines, together with the laser beam 4 and the scattering particles, the effective size of the scattering volume S. Aperture 12 in stop 11 defines the extension of the scattering volume S in the direction of the laser beam, as indicated by the broken lines. The extension of S perpendicular to the beam is determined by the cross section area of the beam. Generally the individual scattering particles are small compared with the extension of S.

A further aperture 13, for example a slit aperture, is disposed between the parabolic mirror 1 and the optical lens 9 in the front focal plane of lens 9. Aperture 11 is spaced from lens 9 by a distance corresponding to its focal length $f_1$ and from lens 10 by a distance corresponding to its focal length $f_2$. Lens 10 itself is spaced from the viewing window 3 of the vidicon 2 by a distance corresponding to its focal length $f_2$.

The angle ($\theta$) is with reference to the direction of the laser beam 4. Thus $\theta = 180°$ corresponds to the top of the scattering volume S and $\theta = 0°$ is diametrically opposed thereto. The angle $\theta$ is the angle between each partial beam, or ray, 5 or 6 and the axis of laser beam 4.

Employing the vertex equation for a parabola, particularly parabola 1, the relationship between the scatter angle $\theta$ and a linear coordinate $s$ as defined in FIG. 1 is as follows:

$$s = \alpha \cdot p \cdot (1 - \sin \theta) / \cos \theta \tag{1}$$

where $p$ is the two times the distance between vertex and focal point of the parabola 1 and $\alpha$ is the image size reduction, or magnification, of telescope 8 and has a value between 0 and 1.

The function $s(\theta)$ is not linear, but this can be easily corrected, particularly when the evaluation is effected with a computer. The function is strictly single-valued, so that it can be concluded that a point $s_0$ on window 3 of the vidicon 2 unequivocally corresponds to a particular angle $\theta$.

The reciprocal resolution capability is given by $$d\theta/\pi = (d\theta/ds) \, ds/\pi \tag{2}$$

Differentiating equation (1) with respect to $s$ and giving the width of the window 3 a value of 1, yields:

$$d\theta/ds = -(1 + \sin \theta)/1 \tag{3}$$

From equation 2 the reciprocal resolution capability is thus:

$$d\theta/\pi = [(1 = \sin \theta)/ 1\pi] \cdot ds \tag{4}$$

This function is, as expected, symmetrical with respect to $\theta = 90°$ and varies in toto by a factor 2. The value of $d\theta/\pi$ is determined by the vidicon property $1/ds \cong$ number of channels. It is a minimum value in the sense that the effective reciprocal resolution capability, which also includes the diameter of the opening 12 of aperture 10 and the geometry of the scattering arrangement, must not become any smaller.

FIG. 2 shows a further embodiment for measuring the scattered light angular dependence and including an image conductor and optical multi-channel anlayzer 2. The arrangement of vidicon 2 with its image window 3 as well as telescope 8 and the collimated beam 7 corresponds to that described in connection with FIG. 1.

Aperture 11 also operates in the same manner as aperture 11 of FIG. 1. The scattering particles in the scattering volume S are again excited by the laser beam 4 whose direction determines the angle direction $\theta = 0°$ to 180°. Two special partial beams, or rays, 5 and 6 are again considered which form the angle $\theta$ with the direction of laser beam 4.

The transformation of the energy current density I ($\theta$) is here effected, however, with the aid of a fiberoptic image conductor 14. The scattered volume S is enclosed by a cylindrical surface 15 whose center of curvature determines the location of volume S. Extending from this cylindrical surface 15 is a plurality of individual light conductive fibers 16 which end on or at a planar surface 17. This surface 17 corresponds approximately to the cross section of the beam 7 which is reproduced on the viewing window 3 of the vidicon 2.

The light conductor bundle 14 with the individual light conductive fibers 16 is arranged so that one fiber which begins at angular position $\theta$ ends at point $s = r (-\pi/2 + \theta) \cdot \theta$ is the scattering angle, $r$ the radius of the cylindrical surface and $s$ a coordinate of a point located on the front end of the vidicon or image intensifier.

The intensity distribution on the planar surface 17 exactly corresponds to the development of the intensity distribution on the cylindrical surface 15; the transformation is linear. The further transmission of the collimated beam 7 is analogous to that described in connection with FIG. 1.

One main advantage of the device according to the present invention resides in the use of a vidicon multichannel device as the analyzer. Such a device is able to record events of as short a duration as desired provided the number of light quanta per channel is sufficient. The time resolution can be given by the duration of the primary light flash, i.e. the duration of the light beam 4, or by electric gating of an image intensifier 18 part integrated in vidicon 2. The laser beam comes e.g. from a commerical gas laser 19. Its cross section together with aperture 12 determines the extension of the scattering volume S, as previously described. The dimensions of the scattering volume S are small compared the parameter $p$ of the parabola or the radius $r$ of the cylindrical surface of the fiberoptics. Characteristic dimensions are of the order: for the area of surface 3 12.5 mm in the direction of $s$ and 9 mm perpendicular to $s$, for the focal lengths of lens 9 and 10 20 cm and 5 cm resp., for the distance between focal point and vertex of the mirror 12.5 mm, for the radius $r$ of the fiberoptics 16 mm, for the aperture 12 a fraction of a millimeter. Aperture 13 is a slit of about 50 mm length and 10 mm height. Short time resolution is achieved either by means of the provided scanning operation of the mentioned Optical Multichannel Analyzer which has a repetition frequency of ca. 30 Hz or by actuating the electrooptical shutter 20 or the image intensifier which in principle allows to define nanosecond time intervals.

It will be understood that the above description of the present invention is susceptible to various modifications, changes and adaptations, and the same are intended to be comprehended within the meaning and range of equivalents of the appended claims.

I claim:

1. Apparatus for rapidly measuring the angular dependence of radiation emanating from a volume disposed at a predetermined location, comprising: a local resolution radiation detector having a radiation-sensitive surface; means directing a laser beam through the volume; and an optical system disposed between the predetermined location and said radiation-sensitive surface to have its optical axis transverse to the axis of the beam, and constituting means creating an unequivocal correspondence between the angular direction of radiation from such volume and the point of impingement thereof on said radiation-sensitive surface.

2. An arrangement as defined in claim 1 wherein said optical system comprises: a parabolic mirror disposed with its focal point coincident with the location of such volume and subtending an angle of about 180° about such location for transforming radiation from such volume into a collimated beam; and a lens system disposed for optically reproducing such collimated beam on said radiation-sensitive surface.

3. An arrangement as defined in claim 1 wherein said optical system comprises: an array of radiation conducting fibers disposed adjacent one another with their input ends lying on a cylindrical surface whose center of curvature corresponds to such location and subtends an angle of about 180° around such location, and with their output ends extending parallel to one another to convert radiation from the volume into a collimated beam, with the radiation intensity distribution in such collimated beam corresponding exactly to the radiation intensity distribution on said cylindrical surface; and a lens system disposed for optically reproducing such collimated beam on said radiation-sensitive surface.

4. An arrangement as defined in claim 3 wherein said fibers are light conductive fibers.

5. An arrangement as defined in claim 1 wherein said radiation detector comprises an electronic shutter for enabling the radiation measurement to be performed during a predetermined time interval.

6. An arrangement as defined in claim 1 further comprising means for pulsing the radiation from the volume in order to limit the radiation measuring time.

7. An arrangement as defined in claim 1 wherein said detector comprises an optical multi-channel analyzer and said radiation-sensitive surface of said detector comprises a plurality of parallel, juxtaposed, slit-type, radiation-sensitive surface elements.

8. An arrangement as defined in claim 7 wherein said radiation-sensitive surface is planar.

* * * * *